(12) United States Patent
Wenzler

(10) Patent No.: US 7,621,932 B2
(45) Date of Patent: Nov. 24, 2009

(54) SURGICAL PUNCHING INSTRUMENT

(75) Inventor: Jörg Wenzler, Hausen ob Verena (DE)

(73) Assignee: Jörg Wenzler Medizintechnik GmbH, Hausen ob Verena (DE)

( * ) Notice: Subject to any disclaimer, the term of this patent is extended or adjusted under 35 U.S.C. 154(b) by 320 days.

(21) Appl. No.: 11/250,025

(22) Filed: Oct. 13, 2005

(65) Prior Publication Data
US 2006/0085021 A1 Apr. 20, 2006

(30) Foreign Application Priority Data
Oct. 14, 2004 (DE) ................. 20 2004 015 990 U

(51) Int. Cl.
A61B 17/32 (2006.01)
(52) U.S. Cl. ..................................... 606/184
(58) Field of Classification Search ................ 606/184, 606/185, 170
See application file for complete search history.

(56) References Cited

U.S. PATENT DOCUMENTS

| 3,692,020 | A | | 9/1972 | Schied |
| 5,273,519 | A | * | 12/1993 | Koros et al. .................... 606/83 |
| 5,312,407 | A | | 5/1994 | Carter |
| 6,142,997 | A | * | 11/2000 | Michelson ................... 606/83 |
| 6,322,579 | B1 | * | 11/2001 | Muller ....................... 606/205 |

FOREIGN PATENT DOCUMENTS

| DE | 356185 | 7/1922 |
| DE | 44 24 659 | 1/1996 |
| DE | 198 52 682 | 5/2000 |

OTHER PUBLICATIONS

Jörg Wenzler Medizin—Technik—GmbH, Feb. 16, 2005, BILLY® I, BILLY® I Laminektomie—Stanzen, zerlegbar.

* cited by examiner

Primary Examiner—(Jackie) Tan-Uyen T. Ho
Assistant Examiner—Gregory A Anderson
(74) Attorney, Agent, or Firm—McGlew and Tuttle, P.C.

(57) ABSTRACT

A surgical punching instrument with a fixed handle (21) is attached to a tubular guide part (20). An actuating lever (23) is mounted on the fixed handle (21) in a pivotingly movable manner and is in connection with a plunger (27) via a short lever arm (24). This plunger is in turn connected to a punching slide (1) and is mounted for actuating same against the action of a compression spring in an axially movable manner in a rearward mounting part (31) of a punching bar (2), which is guided rotatably by an at least partially cylindrical guide section (33, 34) and lockably in different rotated positions in the guide part (20). The punching bar is in contact in the guide part (20) with an axial stop acting in the direction of actuation with a ring shoulder (35) and it is locked in an axially detachable manner. The axial stop, with which the ring shoulder (35) is in contact, comprises a spring-loaded locking lever (37), which passes through a guide slot (45) of the guide part (20) radially into a cylindrical cavity (20') of the guide part (20), in which the guide section (33, 34) of the mounting part (31) of the punching bar (2) is guided.

17 Claims, 2 Drawing Sheets

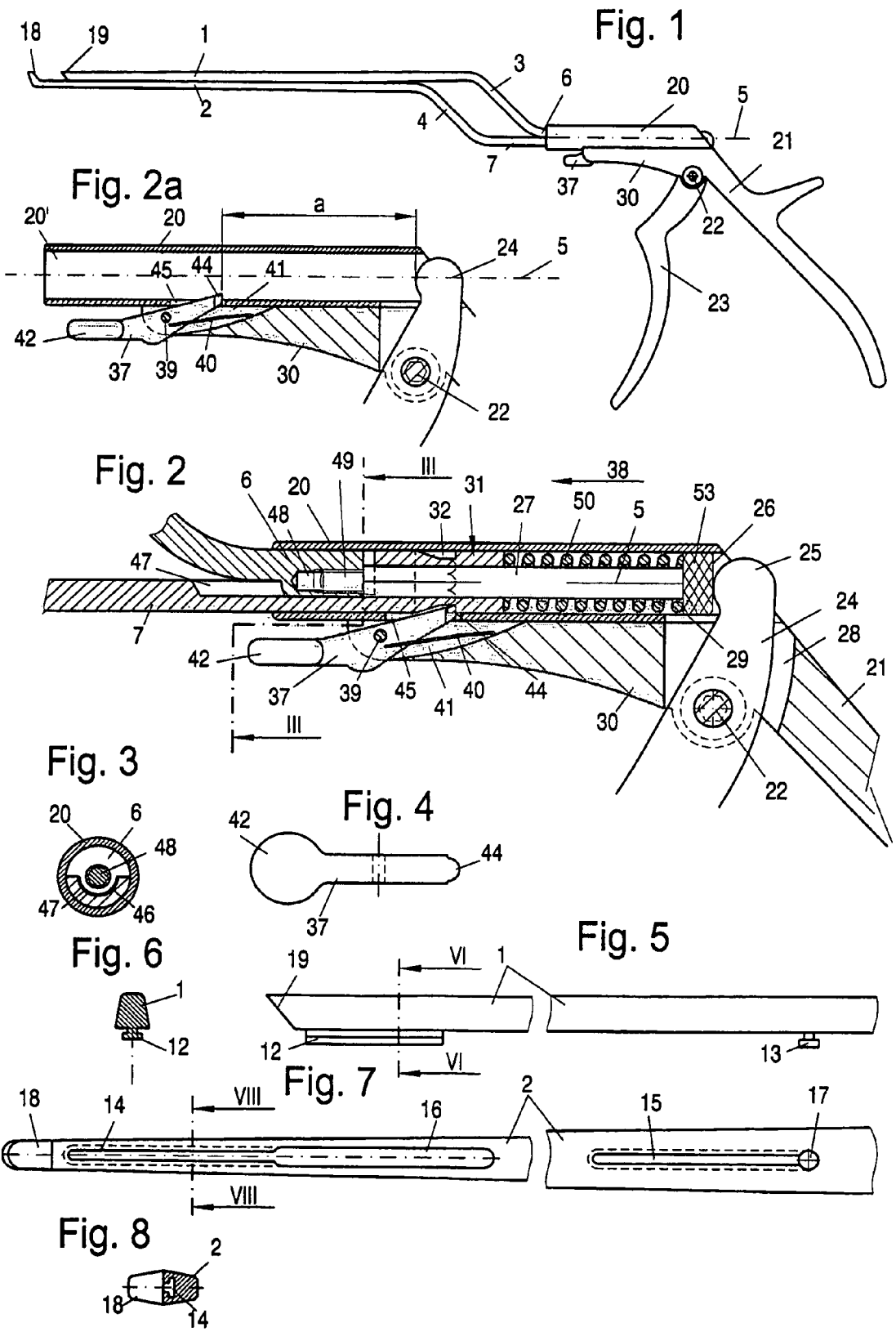

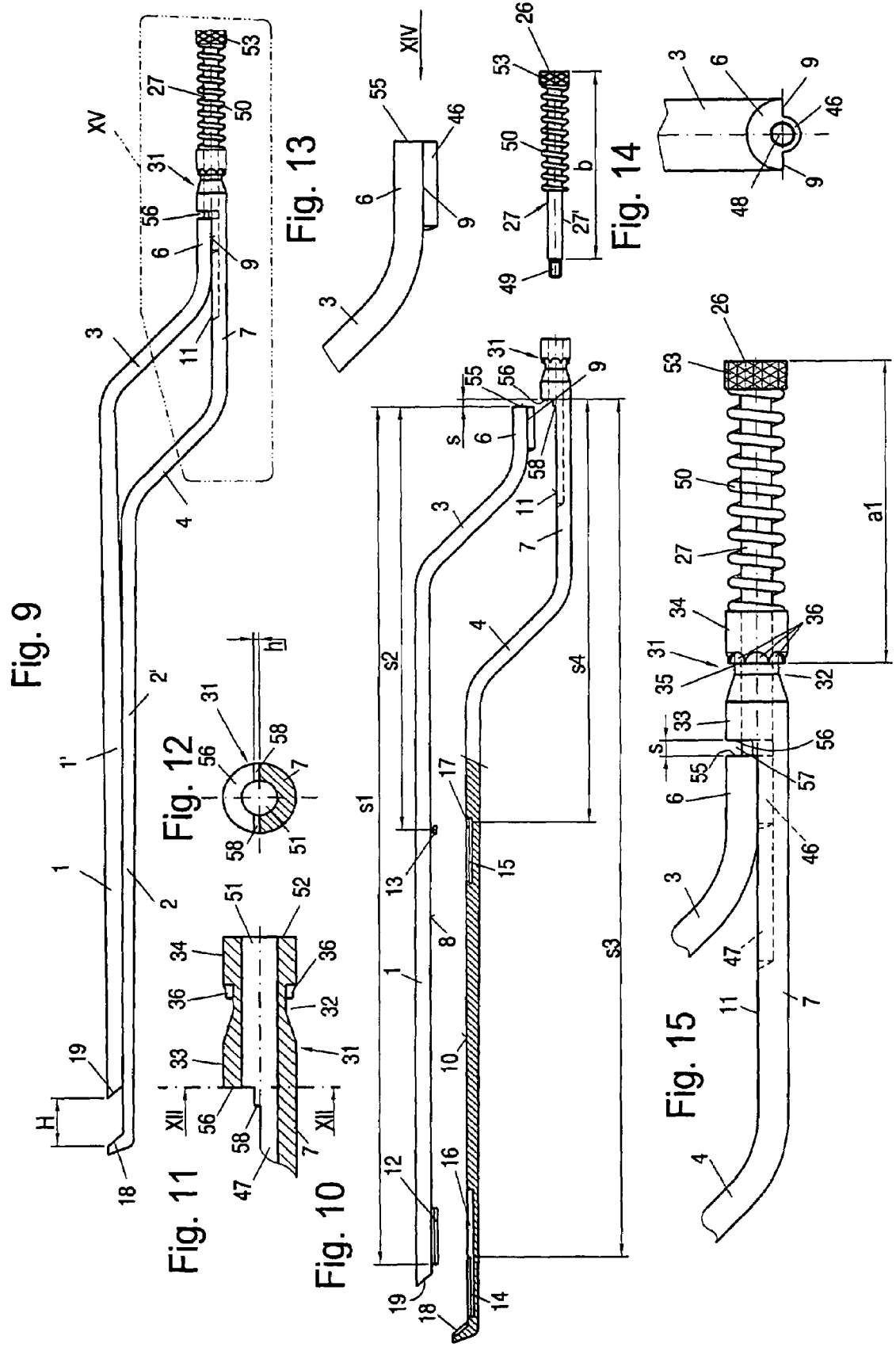

SURGICAL PUNCHING INSTRUMENT

CROSS REFERENCE TO RELATED APPLICATIONS

This application claims the benefit of priority under 35 U.S.C. § 119 of German Patent Application DE 20 2004 015 990.2 filed Oct. 14, 2004, the entire contents of which are incorporated herein by reference.

FIELD OF THE INVENTION

The present invention pertains to a surgical punching instrument with a fixed handle attached to a tubular guide part and with an actuating lever, which is mounted thereon in a pivotingly movable manner and which is in connection via a short lever arm with a plunger, which is in turn connected to a punching slide and is mounted for actuating same against the action of a compression spring in an axially movable manner in a rearward mounting part of a punching bar, which is guided rotatably by means of an at least partially cylindrical guide section and lockably in different rotated positions in the guide part, the punching bar being in contact in the guide part with an axial stop acting in the direction of actuation with a ring shoulder and being locked in an axially detachable manner.

BACKGROUND OF THE INVENTION

A decomposable laminectomy punch, in which the two punch shafts, namely a punching bar and a punching slide, comprise straight, rod-shaped bodies each, which are mutually guided at one another, in the customary manner, by guide elements having a T-shaped profile that engage one another in a positive-locking manner, is known from an inhouse publication of the applicant. The rear end of the punching bar is provided here with a cylindrical mounting part, which has a larger diameter and has on its front side an annular stop shoulder, with which it is in contact with an axial stop, which is designed as a ring shoulder and in which the rearward ends of both punch shafts are mounted.

The movable punching slide is connected in an articulated manner to a pin-like plunger, which passes through a central axial hole of the guide part. At its rear end, this plunger has a pushing head, whose diameter is expanded and at which the short lever arm of the actuating lever for actuating the punching slide acts against the action of a restoring spring designed as a compression coil spring arranged on the plunger when the actuating lever is actuated. Locking depressions for a ball notch, which are arranged in a uniformly distributed manner, are provided on the circumference of the cylindrical mounting part. The two punch shafts can be rotated together in the tubular guide part and locked in a locking manner in different angular positions by means of this ball notch.

To make it possible to remove the two punch shafts together from the guide part, e.g., for cleaning purposes, it is necessary to remove the short lever arm of the actuating lever from the path of motion of the plunger. The actuating lever is mounted for this purpose with the short lever arm radially displaceably in relation to its bearing axis and with a special, axially stepped bearing journal, which can in turn be displaced against spring pressure in a bearing bore. The two punch shafts can then be pulled out of the guide part on the rear side together with the plunger and the restoring spring. These two parts can then be separated from one another by releasing the guide elements profiled in a T-shaped manner by correspondingly displacing the punching slide in the longitudinal direction relative to the punching bar.

This type of decomposability can be applied in case of straight punch shafts only, which can be pushed over their entire length through the tubular guide part. This type of decomposability cannot be used in case of punch shafts bent at right angles.

Another surgical bar shaft instrument, in which both grip parts are fixed together to a tubular guide part in an articulated manner and can be locked, is also known from DE 198 52 682 C2. By releasing the bolted connection, the two lever arms and especially the short lever arm of the actuating lever can be pivoted out of the path of movement of the two punch shafts, so that these can be pulled out of the guide part on the rear side.

This type of decomposability cannot be used in the case of punch shafts having a bent offset portion, which can be offset at right angles, either.

SUMMARY OF THE INVENTION

The basic object of the present invention is to provide a surgical punching instrument of the type mentioned in the introduction, but with instrument shafts that have bent offset portions, which can be bent at right angles, in which the instrument shafts comprising a punching slide and a punching bar each can be inserted into the guide part and can be removed therefrom in a simple manner, e.g., for cleaning purposes.

This object is accomplished according to the present invention by the axial stop, with which the ring shoulder is in contact, comprises a spring-loaded locking lever, which protrudes through a guide slot of the guide part radially into a cylindrical cavity of the guide part, in which the guide section of the mounting part of the punching bar is guided.

With the design according to the present invention, punch shafts bent at right angles can also be mounted snugly in the guide part, rotated, locked in different angular positions and removed in a simple manner. In addition, the design according to the present invention has the considerable advantage that the short lever arm of the actuating lever does not need to be mounted in a radially movable manner and does not need to be able to be removed from the path of motion of the plunger in order to make it possible to remove the punch shafts from the guide part.

Unlike in the prior-art instruments, the punch shafts are inserted into the tubular guide part and removed from the tubular guide part from the proximal side, i.e., from the front.

Another advantage of the design according to the present invention is that it can be readily embodied with straight punch shafts.

Instead of the ball notch means provided in the case of the prior-art instruments, the design according to another aspect of the present invention has the considerable advantage that reliable securing of the punch shafts against rotation can be achieved with it relative to the tubular guide part and the handles, but this securing against rotation can also be easily released, by a corresponding actuation of the locking lever, in order to disengage the latter from the notches of the lever.

The embodiment of the punch shafts, which is bent at right angles and is provided according to another aspect of the invention, is especially advantageous for the surgeon using the instrument, because he can readily recognize the particular angular position in relation to the handles at any time. This is not possible so easily in case of straight punch shafts.

Due to the embodiment according to another aspect of the invention, it is ensured that the engagement between the locking lever and the locking notches of the mounting part of the punching bar is guaranteed even in the inoperative position of the actuating lever, so that an independent rotation of the punch shafts in the guide part is prevented from occurring with certainty.

Due to the embodiment according to another aspect of the invention, it is also ensured with simple means that the two punch shafts do not separate from one another independently when they are removed from the guide part, and the embodiment according to claim 6 offers a simple possibility of removing the punching slide from the punching bar and to reattach it to same.

Another advantageous embodiment is provided according to another aspect of the invention. Due to this embodiment, the plunger can be separated from the punching slide in a simple manner, and it is also possible, to mount and remove the compression spring in a simple manner.

Good guiding of even the distal end section of the punching slide on the punching bar can be achieved with the embodiment according to another aspect of the invention.

Due to the embodiment according to another aspect of the invention, the two punch shafts, which are displaceably connected to one another, receive a good guiding within the tubular guide part with the cylindrical guide hole thereof, whose diameter is coordinated with the guide sections of the bearing part.

An exemplary embodiment of the present invention will be explained in greater detail below on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a side view of a surgical punching instrument;

FIG. 2 is an enlarged sectional view of the tubular guide part of the punching instrument;

FIG. 2a is a sectional view of the empty guide part;

FIG. 3 is a section III-III from FIG. 2;

FIG. 4 is the top view of the locking lever as an individual part;

FIG. 5 is the side view of the straight, front section of the punching slide;

FIG. 6 is a section VI-VI from FIG. 5;

FIG. 7 is a top view of the front section of the punching bar;

FIG. 8 is a section VIII-VIII from FIG. 7;

FIG. 9 is a side view of the two punch shafts with the plunger and the restoring spring;

FIG. 10 is a side view of the two punching slides and the plunger with the restoring spring in a separate view, where the punching bars are shown in a partially cut-away view;

FIG. 11 is an enlarged view of the mounting part of the punching bar;

FIG. 12 is a sectional view XII-XII from FIG. 11;

FIG. 13 is an enlarged side view of the rear end section of the punching bar;

FIG. 14 is a front view XIV from FIG. 13; and

FIG. 15 is an enlarged detail XV from FIG. 9.

DESCRIPTION OF THE PREFERRED EMBODIMENTS

Referring to the drawings in particular, The instrument shown in the drawings is a laminectomy punch with two punch shafts, namely, a punching slide 1 and a punching bar 2, both of which are uniformly bent at right angles and thus have sections 3 and 4, which extend obliquely in relation to the straight shaft sections 1' and 2' and whose rear sections 6 and 7 lie in one another in a slidingly displaceable manner.

It is achieved due to the two oblique sections 3 and 4 of the punching slide 1 and of the punching bar 2 that the two straight sections 1' and 2' of these punch shafts extend radially offset from the axis 5 of the mounting part 20 but in parallel thereto.

While the obliquely extending sections 3 and 4 may have any desired cross-sectional shape, the sections 1' and 2' as well as 6 and 7, which lie one on top of another, are provided with flat sliding surfaces 8 and 9 or guiding surfaces 10 and 11 on the sides facing each other (FIG. 10). In the area of the sliding surface 8, the punching slide 1 is provided with a guide bead 12 profiled in a T-shaped pattern at its front end and with a guide pin 13 profiled in a T-shaped pattern in the middle area. To receive these guide elements 12 and 13, the punching bar 2 is provided with two guide grooves 14 and 15, which are located at correspondingly spaced locations from one another and have a T-shaped profile each. While the guide groove 14 is joined by a broader insertion groove 16 for inserting the guide bead 12, the guide groove 15 is provided at its rear end with a hole 17 for inserting the guide pin 13.

The front end of the punching bar 2 is provided with an upwardly directed punching blade 18, which is designed as an abutment for the punching edge 19 of the punching slide 1.

The punching slide 1 is displaceable on the punching bar 2 by the punching stroke H by actuating the actuating lever 23 via the short lever arm 24.

The two punch shafts 1 and 2 are mounted, in the assembled state, together in a tubular guide part 20 in the manner to be described in greater detail below.

A stationary handle 21, on which an actuating lever 23 is mounted in a pivotingly movable manner by means of a bearing journal 22, is attached to the guide part 20. This actuating lever 23 has a short lever arm 24 with a rounded end section 25, which is in contact with the pressing surface 26 of a plunger 27. The lever arm 24 is mounted in a slot-like recess 28 of the handle 21, and it passes through a slot 29 of the tubular guide part 20. The tubular guide part 20 is arranged snugly on a horizontal bearing shaft 30 of the handle 21 and is welded or soldered to same.

As can be recognized from FIGS. 2 and 3, the guide part 20 comprises a cylindrical tube with a likewise cylindrical cavity 20' (FIG. 2a). The punch shafts 1 and 2 lying on one another with their flat sliding and guiding surfaces 9 and 11 as well as 8 and 10 are mounted in this guide part 20 in the assembled state.

To achieve good, possibly clearance-free guiding for the rear section 7 of the punching bar 2 in the guide part 20, this rear section 7 is provided with a cylindrical mounting part 31. This mounting part 31 has a peripheral, partly conical incision 32, by which the mounting part 31 is divided into two cylindrical guide sections 33 and 34. A radial ring shoulder 35, in which a total of eight locking notches 36 are milled, which are arranged in a uniformly distributed manner in the circumferential direction, is formed by this incision 32.

A locking lever 37 is provided as an axial stop acting in the direction of the arrow 38 for this ring shoulder 35 with the locking notches 36 thereof. By means of a bearing journal 39, the locking lever 37 is mounted pivotably in a recess 41 of the bearing shaft 30 against the action of a leaf spring 40. It has an actuating arm 42, which projects from the recess 41 of the mounting shaft 30 and is located under the front section of the guide part 20.

A second active locking arm 43 of the locking lever 37 engages one of the locking notches 36 of the mounting part 31 with a locking catch 44 adapted to the shape of the locking notches 36 under the action of the spring 40.

By correspondingly actuating the locking lever 37, the locking arm 43, which protrudes into the cavity 20' of the tubular guide part 20 through a slot 45 of the tubular guide part 20, can be disengaged from the ring shoulder 35 and the locking notch 36, so that the punching bar 2 can be pulled out of the guide part 20 in the direction of arrow 38.

As is apparent most clearly from FIG. 3, the rear, i.e., distal end 6 of the punching slide 1 has the cross-sectional shape of a semicylinder, which protrudes into a central longitudinal groove 47 having a U-shaped profile through a semicylindrical attachment 46 of a smaller diameter and creates the possibility of providing a central threaded hole 48 in the end section 6. This threaded hole 48 is used to axially fasten the plunger 27 to the punching slide 1. This plunger 27 is provided for this purpose, at the front end of its cylindrical shaft 27', with a threaded pin 49, which has a somewhat smaller diameter than the shaft 27'. A compression coil spring 50 acting as a restoring spring is arranged on the shaft 27'. To receive the front part of the shaft 27' in a guiding and axially movable manner, the mounting part 31 of the punching bar 2 is provided with a central through hole 51, which continues in the U-shaped, i.e., semicylindrical longitudinal groove 47.

As is apparent from FIG. 2, the compression coil spring 50 is in contact with the rear-side face 52 of the mounting part 31. With the other end, it is supported at a head part 53 of the plunger 27, whose rear-side face 26 forms the pressing surface for the short lever arm 24 of the actuating lever 23. It can be recognized from the drawing that the shaft 27' of the plunger 27 has a smaller diameter than the pressing head 53, whose diameter is adapted to the internal diameter of the guide part 20. The shaft 27' of the plunger 27 passes through the compression coil spring 50 and the central axial hole 51 of the mounting part 31. The circumferential surface of the pressing head 53 is knurled to ensure that the plunger 27 can be screwed easily into the rear end 6 of the punching slide and can be easily detached therefrom.

To guarantee clearance-free mounting of the mounting part 31 in the axial direction in the guide part 20, the axial distance a between the axial stop formed by the locking catch 44 and the short lever arm 24 of the actuating lever 23 should be selected to be at most equal to the distance a1 between the ring shoulder 35 and the rear-side face or pressing surface 26 of the plunger 27 that is in contact with the short lever arm 24. This can be easily accomplished by selecting the length b of the plunger 27 correspondingly.

If this distance a is selected to be somewhat smaller than the distance a1, a certain axial pressure is to be applied against the short lever arm 24 of the actuating lever when the mounting part 31 is inserted into and locked in the guide part 20 in order to enable the locking lever 37 to jump into engagement with the ring shoulder 35 or one of the locking notches 36.

As can be best recognized from FIG. 15, there is an axial gap 57 of the width s between the rear-side face 55 and the face 56 of the guide section 33, which latter face is located opposite the face 55, when the plunger 27 is screwed into the rear end section 6 of the punching slide 1. This gap 57 develops due to the fact that in the mounted state, the face 55 is in contact with two diametrically opposed stop faces 58 (FIG. 12), which project over the guide surface 11 of the rear section 7 of the punching bar 2 by the height h of about 0.5 mm to 1.5 mm. It is thus also ensured that the guide bead 12 and the guide pin 13 cannot leave the guide grooves 14 and 15 as long as the gap 57 exists.

To guarantee this, the distances s1 and s2, which the guide bead 12 and the guide pin 13 have from the rear face 55 of the punching slide, are smaller than the distances s3 and s4 by the dimension s of the gap 57, s3 being the distance between the front guide groove 14 and the front face 56 of the guide section 33 and s4 being the distance between the hole 17 and the face 56. The dimension s may be between about 0.5 mm and 3 mm.

To make it possible to detach the punching slide 1 from the punching bar 2, it is necessary to screw the plunger 27 out of the threaded hole 46 of the rear section 6 of the punching slide 1. Because of the elasticity of the material, it is possible to raise the rear section 6 over the height h of the stop faces 58 in order to move the punching bar 2 farther against the face 56 in order to release the engagement between the guide bead 12 and the guide pin 13, on the one hand, and the guide grooves 14 and 15, on the other hand.

To insert the two punch shafts, which are connected to one another, i.e., the punching slide 1 and the punching bar 2, with the plunger 27 screwed in and with the compression coil spring 50 from the front side into the hole 20' of the guide part 20, it is only necessary to insert this [the guide part] against the direction of the arrow 38 and to press it against the short lever arm 24 until the locking catch 44 of the locking lever 37 is audibly snapped into one of the index notches 36. The instrument is immediately ready for use thereafter.

If another angular position of the punch shafts 1 and 2 in relation to the handles 21 and 23 is to be reached, the locking lever 20 is to be actuated correspondingly in order to release the engagement of its locking catch 44 with one of the index notches. After the two punch shafts 1 and 2 have then been rotated into the desired angular position, the engagement with the locking catch 44 is again established by repeatedly pressing the mounting part 31 against the short lever arm 24. The mounting part 31 can also be released in the same manner for removal from the guide part 20.

However, it is also possible to disengage the locking catch 44 of the locking lever 37 from the locking notches 36 by moving the mounting part 31 against the spring action, i.e., against arrow 38.

While specific embodiments of the invention have been shown and described in detail to illustrate the application of the principles of the invention, it will be understood that the invention may be embodied otherwise without departing from such principles.

What is claimed is:

1. A surgical punching instrument, comprising:
a fixed handle;
a tubular guide part, said fixed handle being attached to said tubular guide part, said tubular guide part defining a cylindrical guide part cavity;
an actuating lever mounted on said fixed handle in a pivotingly movable manner, said actuating lever having a short lever arm;
a plunger, said actuating lever being connected to said plunger via said short lever arm;
a compression spring;
a punching bar having a rearward mounting part, said rearward mounting part having an at least partially cylindrical guide section, said punching bar being guided in said guide part rotatably via said guide section, said punching bar having a ring shoulder, said ring shoulder being located in said guide part, said rearward mounting part being mounted in said cylindrical guide part cavity of said guide part;

a mobile punching slide, said plunger engaging said compression spring, said compression spring resetting said mobile punching slide, said plunger being detachably connected to a rear end of said punching slide such that said plunger moves in an axial direction in said guide part, said plunger compressing said compression spring when said plunger moves in said axial direction, said cylindrical guide part cavity having a dimension equal to or greater than said rearward mounting part such that said rearward mounting part is received by said guide part in a direction opposite a direction of actuation of said mobile punching slide, whereby said mobile punching slide is disconnected from said guide part in said direction of actuation of said mobile punching slide punching slide, wherein said punching bar and said punching slide have guide elements, said guide elements of said punching slide detachably engaging said guide elements of said punching bar such that said guide elements of said punching slide form a positive-lock connection with said guide elements of said punching slide, said punching slide being axially movable along said punching bar, said punching slide and said punching bar having bent portions, said bent portions being located in front of said guide part, wherein said punching slide and said punching bar extend radially offset in relation to an axis of said guide part; and a spring-loaded locking lever defining an axial stop, said locking lever extending radially through a guide slot defined by said guide part such that said locking lever detachably engages said ring shoulder in said cylindrical cavity of said guide part, whereby said ring shoulder is lockable in a plurality of rotated positions, said locking lever locking said mounting part of said punching bar when said locking lever engages said ring shoulder.

2. A surgical punching instrument in accordance with claim 1, wherein said ring shoulder comprises a plurality of locking notches arranged in a distributed manner in a circumferential direction, said locking lever having a locking catch, said locking catch engaging one of said locking notches.

3. A surgical punching instrument in accordance with claim 1, wherein an axial distance defined between said axial stop formed by said locking lever and said short lever arm of said actuating lever is equal to or less than a distance between said ring shoulder and a rear-side face of said plunger, said rear-side face being in contact with said short lever arm.

4. A surgical punching instrument in accordance with claim 1, wherein an end of said punching slide facing said short lever arm of said actuating lever is detachably connected to said plunger and is in contact with a stop face of said guide section of said punching bar when said compression spring is compressed via said plunger, said stop face defining an axial inoperative position.

5. A surgical punching instrument in accordance with claim 4, wherein said end of said punching slide is detached from said plunger such that said punching slide is raised over said stop face to release said stop face from said punching bar.

6. A surgical punching instrument in accordance with claim 4, wherein said punching slide is detachably connected to said plunger via a screw connection.

7. A surgical punching instrument in accordance with claim 5, wherein said punching slide is detachably connected to said plunger via a screw connection.

8. A surgical punching instrument in accordance with claim 4, wherein said plunger includes a cylindrical shaft having a head part at an end thereof, said head part having a diameter that is greater than a diameter of another end of said plunger, said plunger extending through a space defined by said compression spring and through a guide hole defined by said guide section of said punching bar, said compression spring being a coil spring.

9. A surgical punching instrument in accordance with claim 4, wherein said guide section of said punching bar is arranged at an end of a bar section, said bar section having a flat sliding surface, said flat sliding surface being parallel to a guiding surface of said punching bar, said rear part of said punching slide having a flat punching slide surface, said flat punching slide surface engaging said flat sliding surface of said bar section.

10. A surgical punching instrument in accordance with claim 1, wherein a peripheral incision divides said mounting part into two said cylindrical guide sections, said ring shoulder defining a plurality of locking notches, said ring shoulder being located between said two cylindrical guide sections of said mounting part of said punching bar.

11. A surgical punching instrument in accordance with claim 1, wherein said actuating lever pivots from a non-use position to a use position, said plunger having a plunger contact portion, said short arm lever contacting said plunger contact portion such that said plunger contact portion compresses said compression spring when said actuating lever is in said use position.

12. A surgical punching instrument in accordance with claim 11, wherein one end of said compression spring engages said plunger contact portion and another end of said compression spring engages said mounting part, whereby said compression spring is located between said mounting part and said plunger contact portion.

13. A surgical punching instrument, comprising:

a fixed handle;

a tubular guide part, said fixed handle being connected to said tubular guide part, said tubular guide part defining a cylindrical guide part cavity, said guide part defining an axially extending guide slot;

an actuating lever mounted on said fixed handle such that said actuating lever pivots from a non-use position to a use position, said actuating lever having a lever arm portion;

a plunger having a plunger contact portion located at an end thereof, said actuating lever being in contact with said plunger via said lever arm portion, said plunger contact portion being located at a distal end of said tubular guide part when said actuating lever is in said non-use position;

a compression spring, said plunger contact portion of said plunger engaging one end of said compression spring;

a punching bar having a rearward mounting part, said rearward mounting part engaging another end of said compression spring, said rearward mounting part having an at least partially cylindrical guide section, said punching bar being guided in said guide part rotatably via said guide section, said punching bar having a ring shoulder, said ring shoulder being located in said guide part, said rearward mounting part being mounted in said cylindrical guide part cavity of said guide part, wherein said punching bar and said punching slide have guide elements, said guide elements of said punching slide detachably engaging said guide elements of said punching bar such that said guide elements of said punching slide form a positive-lock connection with said guide elements of said punching slide, said punching slide being axially movable along said punching bar, said punching slide and said punching bar having bent portions, said bent portions being located in front of said guide part, wherein said punching slide and said punching bar extend radially offset in relation to an axis of said guide part; and a punching slide, said plunger being detachably connected to a rear end of said punching slide such that said plunger moves in an axial direction in said guide part when said actuating lever is in said use position, said plunger compressing said compression spring when said actuating lever is in said use position, wherein said cylindrical guide part cavity has a dimension such that said mounting part is received by said guide part against a direction of actuation of said punching slide, whereby said punching slide is disconnected from said guide part in said direction of actuation of said punching slide; and a spring-loaded locking lever defining an axial stop, said ring shoulder having a ring shoulder surface defining a plurality of notches, each notch defining a rotational position of said punching bar and said punching slide, said locking lever extending through said cylindrical cavity of said guide part such that said locking lever detachably engages one of said notches of said ring shoulder, whereby said ring shoulder prevents said punching bar and said punching slide from rotating when said locking lever engages one of said notches of said ring shoulder.

14. A surgical punching instrument in accordance with claim 13, wherein an axial distance defined between said axial stop formed by said locking lever and said lever arm portion of said actuating lever is equal to or less than a distance between said ring shoulder and a rear-side face of said plunger, said rear-side face being in contact with said short lever arm.

15. A surgical punching instrument in accordance with claim 13, wherein an end of said punching slide facing said lever arm portion of said actuating lever is detachably connected to said plunger and is in contact with a stop face of said guide section of said punching bar when said compression spring is compressed via said plunger, said stop face defining an axial inoperative position.

16. A surgical punching instrument in accordance with claim 13, wherein said punching slide is detachably connected to said plunger via a screw connection.

17. A surgical punching instrument in accordance with claim 15, wherein said plunger includes a cylindrical shaft, said plunger contact portion being connected to said cylindrical shaft, said plunger contact portion having a diameter that is greater than a diameter of another end of said plunger, said plunger extending through a space defined by said compression spring and through a guide hole defined by said guide section of said punching bar, said compression spring being a coil spring.

* * * * *